United States Patent [19]

Nishioka

[11] Patent Number: 5,028,593

[45] Date of Patent: Jul. 2, 1991

[54] TUFTSIN ANALOGS

[75] Inventor: Kenji Nishioka, Houston, Tex.

[73] Assignee: Board of Regents, The University of Texas System, Austin, Tex.

[21] Appl. No.: 394,361

[22] Filed: Aug. 15, 1989

[51] Int. Cl.$^5$ .......................... A61K 37/02; C07K 5/10
[52] U.S. Cl. ......................................... 514/18; 530/330
[58] Field of Search .......................... 530/330; 514/18

[56] References Cited

U.S. PATENT DOCUMENTS

| | | | |
|---|---|---|---|
| 3,778,426 | 12/1973 | Najjar | 530/330 |
| 4,353,823 | 10/1982 | Chipens et al. | 530/330 |
| 4,390,528 | 6/1983 | Najjar | 424/117 |
| 4,434,095 | 2/1984 | Chipens et al. | 260/112.5 |
| 4,487,726 | 12/1984 | Fujino et al. | 260/543 |
| 4,515,920 | 5/1985 | Erickson | 525/54.11 |
| 4,605,641 | 8/1986 | Bolin et al. | 514/12 |
| 4,612,365 | 9/1986 | Birr et al. | 530/301 |
| 4,687,840 | 8/1987 | Pang et al. | 530/331 |
| 4,711,844 | 12/1987 | Chang | 435/317.1 |
| 4,720,484 | 1/1988 | Vincent et al. | 514/18 |
| 4,720,554 | 1/1988 | Irie et al. | 548/533 |
| 4,734,279 | 3/1988 | Stephan et al. | 424/85 |
| 4,786,737 | 11/1988 | Irie et al. | 548/533 |
| 4,816,449 | 3/1989 | Hahn | 530/330 |

FOREIGN PATENT DOCUMENTS

| | | |
|---|---|---|
| 0225648 | 12/1986 | European Pat. Off. . |
| 0253190 | 6/1987 | European Pat. Off. . |
| 8610608 | 7/1986 | France . |

OTHER PUBLICATIONS

Nishioka, et al., Tuftsin: An Immunomodulating Peptide Hormone and its Clinical Potential as a Natural Biological Response Modifier, (1984), pp. 39–49.

Nishioka, et al., Biochemical and Biophysical Research Communications, 47:172–179, (1972).

*Primary Examiner*—Lester L. Lee
*Attorney, Agent, or Firm*—Arnold, White & Durkee

[57] ABSTRACT

The tuftsin analog Thr-Lys-Leu-Lys has been found to have biological activity superior to that of tuftsin itself.

4 Claims, 2 Drawing Sheets

TUFTSIN ANALOGS

BACKGROUND OF THE INVENTION

The present invention relates to peptides which have immunomodulatory activity. More specifically, it relates to analogs of tuftsin.

An enormous number of factors are undoubtedly involved in vivo in the regulation of the immune system, and also in the growth and differentiation of normal and tumor cells. Tuftsin is one such natural immunomodulating factor, and its chemical structure has been established to be L-Thr-L-Lys-L-Pro-L-Arg. Tuftsin has been found to have a number of interesting biological activities, such as antitumor, anti-infection, anti-AIDS and growth factor activities, and enhancement of the phagocytic and cytotoxic activities of leukocytes.

The biological activities of tuftsin have led researchers to attempt to find analogs which have improved activity in one or more respects. Unfortunately, such attempts have been largely unsuccessful. Most of the analogs synthesized either have not possessed the desired activity, or have been found to be competitive inhibitors of tuftsin.

Therefore, a need exists for tuftsin analogs which have advantages in biological activity or in other respects over tuftsin.

SUMMARY OF THE INVENTION

The present invention relates to a peptide which has the amino acid sequence Thr-Lys-Leu-Lys, and pharmaceutically acceptable salts thereof. The present invention also relates to pharmaceutical compositions which include a peptide having the above sequence and a pharmaceutically acceptable carrier.

The present invention is useful as an immunoaugmenting agent with growth factor activity to the treatment of, and for prophylactic treatment of, cancer and infections including AIDS, sickle cell anemia-related infections, post-splenectomy sepsis, post trauma infections, systemic lupus erythematosus-related infections, therapy-induced immune suppression, continuous ambulatory peritoneal dialysis-related infections and tuftsin abnormality disease. The present invention has greater biological activity than tuftsin and is easier to synthesize.

DETAILED DESCRIPTION OF A SPECIFIC EMBODIMENT

Chemical Synthesis

Figure 1:
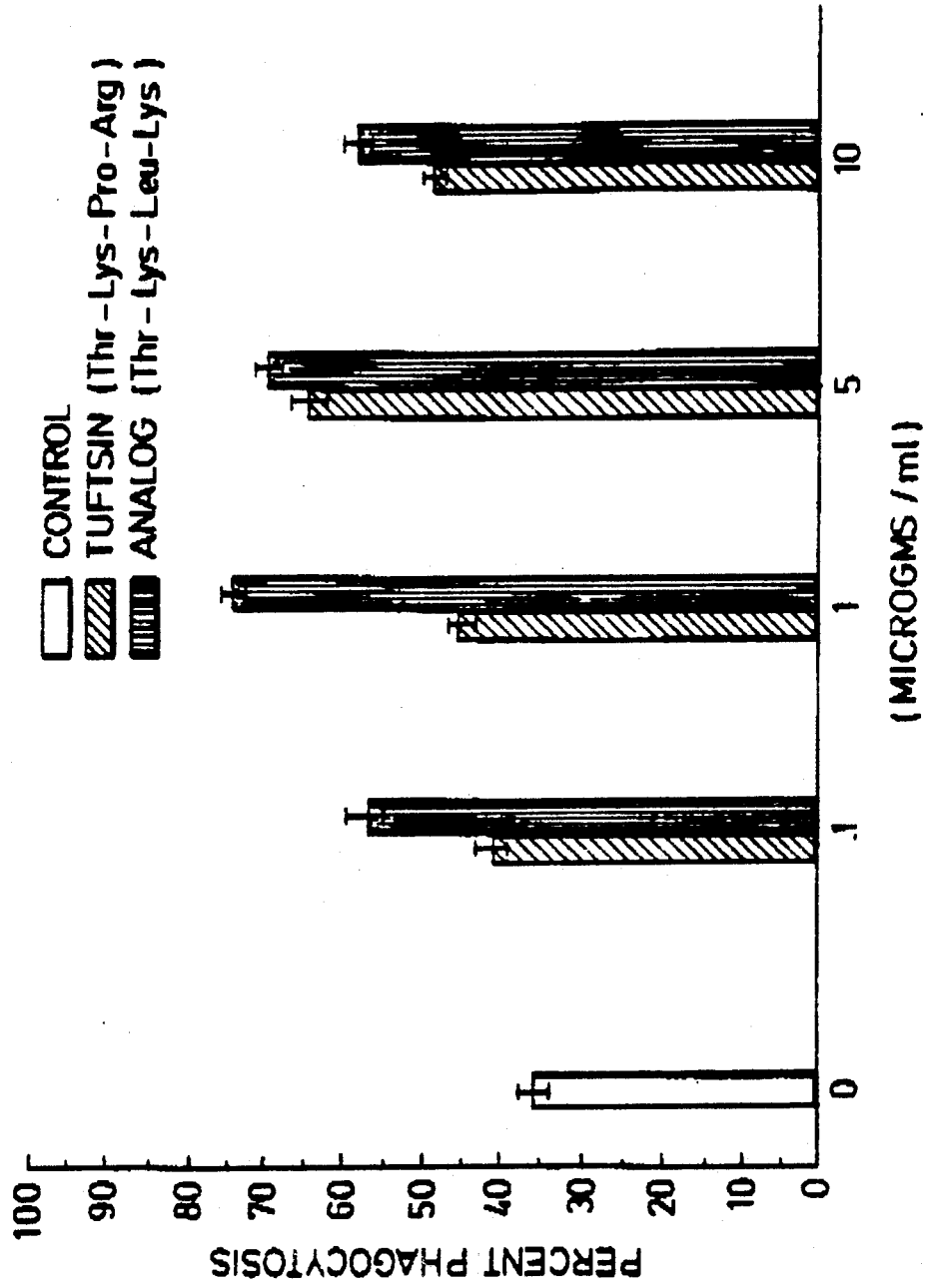
FIG. 1 is a comparison of the ability to stimulate phagocytosis of a control, tuftsin, and a tuftsin analog of the present invention.

L-Thr-L-Lys-L-Leu-L-Lys can be synthesized by any of a wide variety of procedures now available for the chemical synthesis of peptides and proteins. The following are three examples of this synthesis: In the classic solid phase method, Boc-Lys(Z)-OH is esterified to chloromethyl-resin (polystyrene divinyl benzene chloromethyl resin) by preparing the cesium salt of Boc-Lys(Z)-OH and reacting it with the resin in DMSO at 50° C. Resin is filtered and washed with DMSO, DMSO-water, DMSO, methanol and DCM. After drying the resin under a vacuum, acid hydrolysis followed by amino acid analysis of this resin reveals the extent of attachment of Boc-Lys(Z)-OH to the resin (mmoles of lysine per g resin). The coupling of in-coming protected amino acid is performed in a reaction vessel with 15 ml of DCM per g of resin. To achieve the coupling of leucine to lysine, the Boc group of lysine is removed by treatment with 40% TFA in DCM for 20 min. After washing the resin with DCM, the resin is neutralized with 5% EPA in DCM, and washed with DCM. The coupling of leucine is carried out with 2 equivalents of Boc-Leu-OH in the presence of 2 equivalents of DCC for 2 hours. The resin is washed with 10% ethanol in DCM and with DCM. Deblocking of the Boc group and neutralization are performed as before. The coupling of lysine is done by introducing Boc-Lys(Z)-OH in DCM. Since the coupling rate of threonine is slow, Boc-Thr-OH is reacted for 2.5 hours. The resin is then treated with 40% TFA to eliminate the Boc group and non-covalently bound Boc-Thr-OH. After drying the resin under vacuum, the peptide is cleaved off the resin and deprotected with HBr in TFA for 90 min. The peptide in the liquid phase is collected by filtration and washing the resin with TFA, concentrated, precipitated with ethyl ether, and dried under vacuum.

In the classic solution method, Z-Thr-Lys(Z)-Leu-Lys(Z)-OBzl is synthesized by coupling Boc-Leu-OH with H-Lys(Z)-OBzl in the presence of DCC to form Boc-Leu-Lys(Z)-OBzl. To this dipeptide, Boc-Lys(Z)-OH and Z-Thr-OH are coupled in this sequence as active esters (HOBt plus DCC). After each coupling step, the product is purified by extraction (sodium bicarbonate, citric acid) and the protecting groups removed by hydrogenolysis.

In the Fmoc solid phase synthesis method, Fmoc-Lys(Boc)-OH is esterified to p-benzyloxybenzyl alcohol resin by suspending the resin in DCM and adding Fmoc-Lys(Boc)-OH, DMAP and DCC with exclusion of moisture. The resin is washed with DMF, ethanol and DCM, dried under a vacuum, and analyzed for amino acid content. The resin is washed with 25% piperidine in DMF to effect removal of the Fmoc protecting group. After washing with DMF, 2.5 equivalents of the benzotriazole active ester of Fmoc-Leu-OH in 4:1 DMF:DCM is added to the H-Lys(Boc)-resin. The active ester, Fmoc-Leu-OBt, is prepared from the reaction of DCC with Fmoc-Leu-OH in the presence of HOBt in 1:1:1 ratio. After a 50 min. coupling reaction, the cycle is repeated using Fmoc-Lys(Boc)-OBt and Fmoc-Thr(t-Bu)-OBt, 2.5 equivalents each with coupling times of 50 and 90 min., respectively. After removal of the Fmoc group of threonine with 25% piperidine in DMF, the peptide resin is washed with DMF and DCM, and dried under a vacuum. Deprotection of the side chains and cleavage of the peptide from the resin is accomplished in 90% TFA with anisole, thioanisole and 1,2-ethanedithiol added as scavengers. The crude peptide is concentrated, and precipitated from the viscous residue by the addition of ether.

Purification Procedure

The peptide is converted to acetate salt by passing through an Amberlite IRA-400 column (acetate form) and concentrated. This peptide is then purified by eluting the peptide from a CM-cellulose column with increasing concentration of ammonium carbonate buffer pH 7.5, and concentrated. This peptide preparation, after lyophilization, is further purified using high-performance liquid chromatography (C-18 column) using 0.1 M $NH_4H_2PO_4$ with increasing concentration of methanol to eliminate possible minor racemized molecules. Excess ammonium phosphate is removed at this point by passing the peptide through a P-2 gel column in 50 mM acetic acid-ethanol (5%). Since the peptide is still in phosphate salt form, it is converted to acetate form by passage through an Amberlite IRA-400 column (acetate form), and lyophilized.

Abbreviations

Boc: t-butyloxycarbonyl
Bzl: benzyl
CM: carboxymethyl
DCC: dicyclohexylcarbodiimide
DCM: dichloromethane
DMAP: 4-dimethylaminopyridine
DMF: dimethylformamide
DMSO: dimethyl sulfoxide
EPA: N-ethyldiisopropylamine
Fmoc: 9-fluorenylmethyloxycarbonyl
HOBt: 1-hydroxybenzotriazole
Leu: leucine
Lys: lysine
t-Bu: t-butyl
TFA: trifluoroacetic acid
Thr: threonine
Z: benzyloxycarbonyl

Phagocytosis Assay

Human polymorphonuclear leukocytes (PMN) are prepared from venous blood of healthy donors. Heparinized blood is mixed with dextran and kept at 37° C. for 1 hour. The leukocyte-rich plasma is collected and centrifuged. The resulting pellet is washed with Hank's balanced salt solution (HBSS). The pellet is then suspended into HBSS, layered over Lymphocyte Separation Medium (LSM) and centrifuged. The sedimented cells are washed with HBSS. Contaminant erythrocytes are lysed by suspending the cells in sterile water for 15 seconds. The isotonicity is then restored by adding 10XHBSS. After centrifuging, the PMN are washed with HBSS, suspended in the same medium, counted, and adjusted to $1 \times 10^6$ viable cells/ml (viability>95% by trypan blue dye exclusion). Cells ($0.5 \times 10^6$ cells/well) are plated in 24 well plate and placed in a 37° C. $CO_2$ incubator for 30 min. to form a monolayer. Thereafter the supernatant is aspirated. Tuftsin or analog in 250 $\mu$l HBSS and $1.25 \times 10^7$ fluorescent microspheres (2 $\mu$m diameter) in 250 $\mu$l HBSS, are added to each well resulting in a particle to PMN ratio of 25:1, mixed, and incubated for 15 min. The supernatant is then quickly aspirated and each well washed with HBSS. One ml of trypsin (0.25% in saline) is added to each well and the plate incubated for 15 min to detach the cells and remove non-engulfed particles associated on the surface of PMN. The cells are transferred, layered over 2 ml fetal bovine serum (FBS), and centrifuged. The supernatant containing free particles are removed. The cell pellet is suspended, fixed in 2% paraformaldehyde, and plated again into a well. After 10 min, % phagocytosis (% of PMN containing one or more particles) is counted under a microscope. The mean values from triplicates are used. Results are shown in FIG. 1.

Thymidine Incorporation Assay

Figure 2:
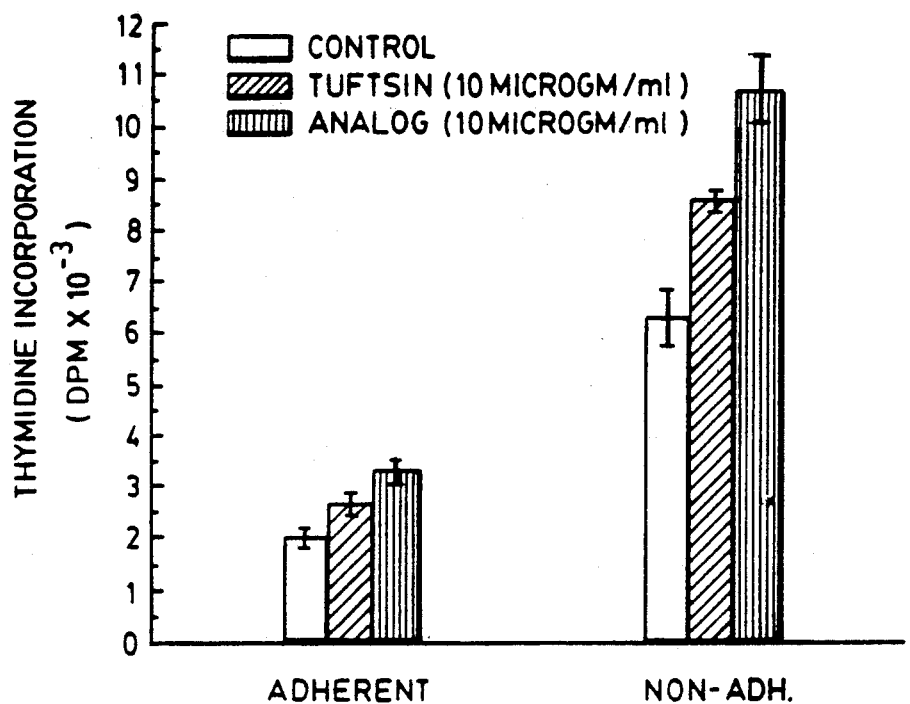
FIG. 2 shows the results of a thymidine incorporation assay (growth stimulation effect) using the same substances.
Figure 3:
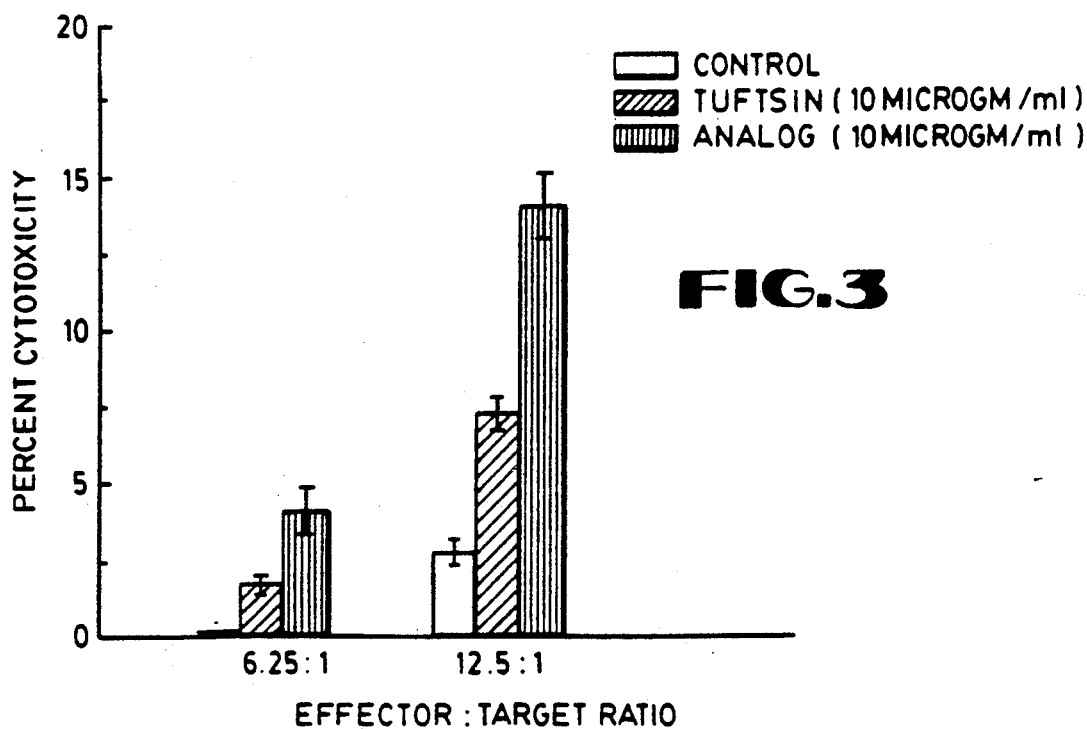
FIG. 3 shows the results of a tumor cell cytotoxicity assay of the same substances.

Spleen is obtained from C57BL/6 female mouse (approximately 3 months old). Splenocytes are prepared by teasing the spleen and passing them through a sieving screen. These cells in HBSS with 2% FBS are then layered over LSM and centrifuged. The cells at interphase are collected, washed with RPMI-1640 medium with 2% FBS, suspended in the same medium at $1 \times 10^6$ cells/ml, and plated into wells ($1 \times 10^6$ cells per well). The plate is incubated for 45 min. in the incubator. Non-adherent cells in each well are transferred to a new well. Adherent cells and non-adherent cells are incubated in separate wells with peptide (10 $\mu$g/ml) for 6 hours in 1 ml RPMI-1640 medium with 2% FBS. $^3$H-thymidine (0.1 $\mu$Ci per well) is then introduced. The plate is kept in the incubator for another 18 hours. Each well is washed and cells are collected into a tube using 1 ml of cold HBSS. After washing the cells twice, the cells are counted, mixed with 0.2 ml of 0.1% sodium dodecyl sulfate, and transferred to a liquid scintillation vial for determination of radioactivity. Results are shown in FIG. 2.

Tumor Cell Cytotoxicity Assay by Human Natural Killer (NK) Cells

A leukocyte-rich buffy coat preparation obtained from leukophoresis of a normal volunteer is used. Buffy coat is diluted with HBSS, layered over LSM, and centrifuged. The mononuclear cells at interphase are collected, washed with HBSS, suspended in RPMI-1640 medium with 10% FBS, adjusted to $5 \times 10^6/1$ ml, plated on Petri dishes (10 ml each), and incubated for 1 hour. Non-adherent cells are collected, poured into bottles containing nylon wool wet with HBSS, and kept in the incubator for 1 hour. Non-adherent cells are collected, suspended in RPMI-1640 medium with 10% FBS, adjusted to $2 \times 10^7$/ml, mixed (1:1 volume ratio) with sheep red blood cells ($6 \times 10^8$/ml), placed in 29° C. bath for 15 min., centrifuged, and again placed in 29° C. bath for another hour. Cell clumps are gently broken up, layered over LSM, and centrifuged. The cells at the interphase are collected, washed with RPMI-1640 medium with 10% FBS, suspended in the same medium, adjusted to $1 \times 10^6$/ml, and kept refrigerated overnight to use for 4 hour $^{51}$Cr release assay.

The viability of this NK cell enriched fraction is assessed with trypan blue, and washed with RPMI-1640 medium with 5% FBS. The tumor target cells, K-562, are harvested from culture and washed with RPMI-1640 medium with 5% FBS and centrifuged. Pelleted cells of $2 \times 10^6$ K-562 are suspended into 0.2 ml of 400 $\mu$Ci of $^{51}$CrO$_4$ in saline, and labelled for 90 min. in 37° C. water bath. The labelled target cells are washed with RPMI-1640 medium with 5% FBS, suspended in the same medium, and adjusted to a suspension of $5 \times 10^4$/ml. These cells are plated to each well ($5 \times 10^3$ cells/0.1 ml) of a 96-well round-bottom microtiter plate. A portion of NK cell-enriched fraction is activated for 1 hour at 37° C. in the presence of 10 $\mu$g peptide per ml of RPMI-1640 medium with 5% FBS and washed with RPMI medium. After adding appropriate numbers of these activated cells are added to each well, a plate is centrifuged for 5 min, and incubated for 4 hours. The plate is removed and centrifuged. Supernatants are absorbed into filter strips and collected using the Skatron Supernatant Collection System. Filters containing radioactive supernatants are counted on a $\gamma$ counter and counts per minutes (cpm) are recorded. Percent cytotoxicity (% specific lysis) is calculated by the following formula:

$$\frac{\text{Experimental cpm} - \text{Spontaneous cpm}}{\text{Maximum cpm} - \text{Spontaneous cpm}} \times 100$$

Spontaneous cpm is obtained by incubating the tumor target cells alone in the medium. Maximum cpm is obtained by releasing the radioactivity from the target cells by treatment with Triton X-100. To summarize the results of the assays described above, the tuftsin analog of the present invention showed significantly greater stimulation of phagocytosis at lower concentrations compared to tuftsin itself. Statistically significant differences were observed at peptide concentrations of 0.1, 1.0, and 10 μg/ml. Further, the analog demonstrated significantly greater activity in stimulating thymidine incorporation (growth stimulation) than did tuftsin. Also, the analog demonstrated significantly greater tumor cell cytotoxicity enhancement of human NK cells.

Pharmaceutical formulations in accordance with the present invention can include the analog of the present invention and a pharmaceutically acceptable carrier. For example, the peptide could by lyophilized in vials and reconstituted in injectable saline for intravenous injection. The present invention can suitably be administered to a patient in an effective amount, through a parenteral method, such as intravenous, intraarterial, intramuscular, intralymphatic, intraperitoneal, subcutaneous, intrapleural or intrathecal injection, or through oral formulations.

The preceding description has been intended to illustrate the present invention, not to provide an exhaustive list of all possible embodiments of the present invention. Those skilled in this field will recognize that modifications could be made which would remain within the scope of the present invention.

I claim:

1. A peptide having the amino acid sequence Thr-Lys-Leu-Lys and pharmaceutically acceptable salts thereof.

2. A peptide having the amino acid sequence L-Thr-L-Lys-L-Leu-L-Lys and pharmaceutically acceptable salts thereof.

3. A pharmaceutically composition, including:
   (a) a pharmaceutically effective amount of a peptide having the amino acid sequence Thr-Lys-Leu-Lys and pharmaceutically acceptable salts thereof; and
   (b) a pharmaceutically acceptable carrier.

4. The composition of claim 3, where the peptide has the sequence L-Thr-L-Lys-L-Leu-L-Lys.

* * * * *

UNITED STATES PATENT AND TRADEMARK OFFICE
CERTIFICATE OF CORRECTION

PATENT NO. :   5,028,593
DATED      :   July 2, 1991
INVENTOR(S) :  Kenji Nishioka It is certified that error appears in the above-identified patent and that said Letters Patent is hereby corrected as shown below:

At column 1, line 3, insert the following --This invention was made with government support under Grant No. R01 CA45730 awarded by the National Cancer Institute. The government has certain rights in the invention.--

Signed and Sealed this

Twenty-fifth Day of May, 1993

Attest:

MICHAEL K. KIRK

Attesting Officer

Acting Commissioner of Patents and Trademarks